United States Patent [19]

Arison et al.

[11] Patent Number: 5,215,894

[45] Date of Patent: Jun. 1, 1993

[54] BIOLOGICAL PROCESS FOR PRODUCING 17β-N-MONOSUBSTITUTED CARBAMOYL-11-OXO-4-AZA-5-α-ANDROST-3-ONE TESTOSTERONE-5-α REDUCTASE INHIBITORS

[75] Inventors: Byron H. Arison, Watchung; Josephine R. Carlin, North Brunswick; Edamanal S. Venkataramani, Somerset, all of N.J.

[73] Assignee: Merck & Co., Inc., Rahway, N.J.

[21] Appl. No.: 841,923

[22] Filed: Feb. 25, 1992

[51] Int. Cl.[5] ............... C12P 33/20; C12P 33/10; C12R 1/89

[52] U.S. Cl. .................. 435/53; 435/60; 435/946

[58] Field of Search .............. 435/53, 60, 946, 59

[56] References Cited

U.S. PATENT DOCUMENTS

| | | |
|---|---|---|
| 2,602,769 | 7/1952 | Murray et al. |
| 2,721,163 | 10/1955 | Shull et al. ............... 435/60 |
| 3,203,869 | 8/1965 | Casas-Campillo ........ 435/60 |
| 3,352,760 | 11/1967 | Vezina et al. ............. 435/60 |
| 4,035,236 | 7/1977 | Wovcha. |
| 4,175,006 | 11/1979 | Wovcha. |
| 4,361,558 | 11/1982 | Wieland et al. |
| 4,430,270 | 2/1984 | Preuss. |
| 4,431,736 | 2/1984 | Rosmesser. |
| 4,614,616 | 9/1986 | Petzoldt et al. |
| 4,732,897 | 3/1988 | Cainelli et al. |
| 4,760,071 | 7/1988 | Rasmusson et al. |
| 4,970,204 | 11/1990 | Holt et al. |
| 5,004,695 | 4/1991 | Jekkel nee Bokany et al. |
| 5,032,586 | 7/1991 | Metcalf et al. |
| 5,041,433 | 8/1991 | Holt et al. |
| 5,120,840 | 6/1992 | Weintraub et al. ............... 540/94 |

OTHER PUBLICATIONS

Venkatarmani et al., American Chem. Society, Biotransformation of Finasteride, vol. 32, No. 1.
Holt et al., J. Med. Chem. 33, 945 (1990).
Rasmusson et al., J. Med. Chem. vol. 29 No. 11 p. 2299 (1986).

*Primary Examiner*—Herbert J. Lilling
*Attorney, Agent, or Firm*—Charles M. Caruso; Robert J. North; Monte R. Browder

[57] ABSTRACT

The present invention is concerned with a novel biotransformation process for producing 17β-N-monosubstituted carbamoyl-11-oxo-4-aza-5-α-androst-3-ones of the formula:

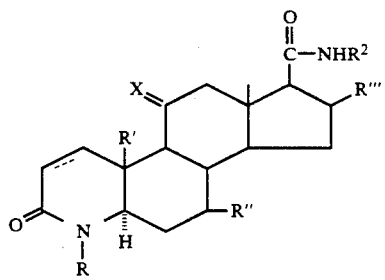

I

These compounds are testosterone 5-α reductase inhibitors and are produced via a claimed novel biotransformation process using the green algae, *Selenastrum capricornutum*.

7 Claims, No Drawings

BIOLOGICAL PROCESS FOR PRODUCING 17β-N-MONOSUBSTITUTED CARBAMOYL-11-OXO-4-AZA-5-α-ANDROST-3-ONE TESTOSTERONE-5-α REDUCTASE INHIBITORS

BACKGROUND OF THE INVENTION

The present invention is directed to a biological or biotransformation process for producing 11α-hydroxyl derivatives of 17β-N-mono-substituted carbamoyl-4-azasteroid compounds using the green algae, *Selenastrum capricornutum*.

The art reveals that a number of microorganisms selected from fungi and bacteria have been used in biotransformation processes to produce biotransformed products. U.S. Pat. No. 4,431,736 describes the production of phenylhydroquinone from biphenyl by biotransformation with selected fungi. This reference specifically describes the microbiological oxidation of biphenyl to bis-hydroxlated biphenyl employing the fungal organism, *Thamnostylum piriforme*.

U.S. Pat. No. 4,397,947 describes a microbial process for 9α-hydroxylation of steroids using the organism, *Nocardia canicruria*. It is known that the microorganisms Achromobacter, Bacillus, Brevibacterium, Corynebacterium, Flavobacterium, Microbacterium, Micybacterium, Protaminobacter, Serratia, and Streptomyces may grow on steroid compounds and degrade the ring system in a non-specific or specific manner. See U.S. Pat. Nos. 4,320,195; 4,175,006; 4,035,236; 4,029,549; 5,004,695. Nocardia species have also been used to hydroxylate non-steroidal compounds. See U.S. Pat. Nos. 4,537,859; 4,582,804. U.S. Pat. No. 2,602,769 describes the 11-hydroxylation of a steroid compound using the fungal microorganism, Rhizopus sp.

The art also reveals that certain undesirable physiological manifestations including acne vulgaris, seborrhea, female hirsutism, male pattern baldness and benign prostatic hypertrophy are the result of hyperandrogenic stimulation induced by excessive accumulation of testosterone or similar androgenic hormones. Early attempts to provide chemotherapeutic agents to counter the unwanted physiological effects of hyperandrogenicity resulted in the discovery of several steroidal anti-androgens that unfortunately had hormonal side effects. For example, the estrogens counteract the effects of androgens but also have a feminizing effect. Non-steroidal anti-androgens such as 4'-nitro-3'-triflouromethylisobutylanilide have also been developed. See Neri et al., Endo., 91, (2), (1972). These compounds may be peripherally active and compete for androgenic receptor sites which could feminize a male host or the male fetus of a female host.

It more recently became known in the art that the princial mediator of androgenic activity in some target organs is 5α dihydrotestosterone which is formed locally in the target organ with the catalytic assistance of the enzyme testosterone-5α-reductase. It therefore has been postulated and demonstrated that inhibitors of testosterone-5α-reductase prevent or diminish the symptoms of hyperandrogenism. See Nayfe et al., Steroids, 14, 269 (1969) and Voight et al., Endocrinology, 92, 1216 (1973). It has also been demonstrated that topical application of either testosterone or 5α-dihydrotestosterone causes enlargement of the female hamster flank organ, an androgen dependent sebaceous structure. However, concomitant administration of 4-androsten-3one-17beta-carboxlyic acid or its methyl ester inhibited the response elicited by testosterone but did not inhibit the response elicited by 5α-dihydrotestesterone. These results indicated that these particular compounds were antiandrogenic because they inhibited testosterone-5α-reductase. Since this discovery, a number of steroidal 5α-reductase inhibitors have been found. See, U.S. Pat. Nos. 5,032,586; 5,026,882; 5,017,568; 4,970,205; 4,970,204; and 4,954,446.

A number of steroidal derivatives with a hydroxyl functionality at the 11 position (either alpha or beta) are known. See, for example, U.S. Pat. Nos. 4,361,558; 4,430,270; 4,432,905; 4,446,072; and 4,448,725. Steroidal derivative(s) with a hydroxyl functionality at the 11 position which inhibit 5α-reductase are known. See U.S. Pat. No. 5,041,433.

A number of 4-aza steroid compounds are known. See, for example, U.S. Pat. Nos. 2,227,876; 3,239,417; and 3,264,301; French Pat. No. 1,465,544; Doorenbos et al., J. Pharm. Sci., 62, (4), 638–640 (1973); J. Pharm. Sci., 60(8), 1234–1235 (1971); J. Pharm Aci., 63(4) 620–622 (1974).

In addition, U.S. Pat. Nos. 4,377,584; 4,220,775; 4,859,681; and the articles J. Med. Chem., 27, 1690-1701 (1984) and J. Med. Chem., 29, 2998-2315 (1986) by Rasmussen et al. and U.S. Pat. Nos. 4,845,104 and 4,732,897 disclose 4-aza-17β-substituted- 5α-androstan-3-ones which are said to be useful in the treatment of hyperandrogenic conditions. Several other U.S. patents refer to aza-steroids including U.S. Pat. Nos. 5,061,802 (17β-aminibenzoyl-4-aza-5α-androst-1-en-3-ones) and 5,049,562 (17β-Acyl-4-aza-5α-androst-1-ene-3-ones).

U.S. Pat. No. 4,760,071 specifically refers to the compound 17β(N-t-butylcarbamoyl)-4-aza-5α-androst-1-en-3-one. Heretofore, however, the art has not referred to any oxidized 4-azasteroids produced via a biotransformation process using the green algal organism *Selenastrum capricornutum* nor to a biological process for the production of the novel compound 17β(N-t-butylcarbamoyl)-11α(hydroxyl)-4-aza-5α-androst-1-en-3-one, which has been found to be an inhibitor of testosterone prostatic 5-α-reductase. The compounds described in this invention are produced via biotransformation in the ubiquitous green algae, *Selenastrum capricornutum*. Use of this organism as an environmental barometer of pollutants is known. See Eirkson et al., "Environmental Assessment Technical Assistance Handbook", Government Publication No. PB87-175345, National Technical Information Service (1987). There is a need, however, for a process that converts steroidal compounds to oxygenated or hydroxylated compounds. This invention claims and describes use of a green algal microorganism to oxidize or hydroxylate steroidal compounds.

SUMMARY OF THE INVENTION

The present invention is concerned with a novel biotransformation process for producing 11-hydroxy 17β-N-(monosubstituted)-carbamoyl-4-aza-5α-androst-1-en-3-one compounds using the green algal microorganism *Selenastrum capricornutum*. These compounds are useful as testosterone 5α-reductase inhibitors to treat various hyperandrongenic conditions including acne vulgaris, seborrhea, female hirsutism, male pattern baldness, and benign prostatic hypertrophy. This novel process may be used to oxidize or biologically transform steroids or steroidal compounds and advantageously may be used to oxidize or hydroxylate 4-azasteroids. Advantageously, this process may also be used to modify or diminish the biological activity of highly active testosterone 5-α reductase inhibitors under circumstances where environmental release is a concern.

Steroids are generally defined as lipids which belong to a family of saturated or unsaturated hydrocarbons containing a minimum of seventeen carbon atoms arranged in a system of four fused rings. The hormones of the gonads and adrenal cortex and the bile acids are biological examples. 4-azasteroids as defined in this specification are a subclass of steroidal compounds in general and have a nitrogen atom rather than a carbon atom at the 4 position of the steroidal structure. This basic ring structure can be further modified as indicated in the specification. Steroidal compounds encompass steroids and 4-azasteroids. The process claimed in the instant invention may be used to modify either steroids or 4-azasteroids to produce an oxidized or hydroxylated product.

The present invention is concerned with a process for biotransforming steroids or 4-azasteroids using the green algal microorganism Selenastrum capricornutum. Advantageously, compounds of the formula:

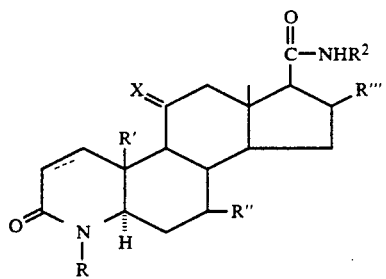

wherein the dashed line indicates a double bond which may be present;

R is hydrogen, methyl or ethyl.

$R^2$ is a hydrocarbon selected from straight and branched chain alkyl of from 1-12 carbons or monocyclic aryl optionally containing 1 or more lower alkyl substituents of from 1-2 carbon atoms and/or more halogen (Cl, F or Br) substituents.

R' is hydrogen or methyl,

R" is hydrogen or β-methyl,

R'" is hydrogen, α-methyl or β-methyl.

X is H, ($OR^3$) wherein $R^3$ is H, $C_{1-13}$ alkyl or aryl is produced using the biostransformation process claimed in the instant invention. More advantageously, the compound 17β(N-t-butylcarbamoyl)-11α-(hydroxyl)-4-aza-5α-androst-1-en-3-one is produced using the green algal organism Selenastrum capricornutum.

DETAILED DESCRIPTION OF THE INVENTION

The present invention is concerned with a novel biotransformation process for producing 11-hydroxy 17β-N-(monosubstituted)-carbamoyl-4-aza-5α-androst-1-en-3-one and androstan-3-one compounds using the green algal microorganism Selenastrum capricornutum. These compounds are useful as testosterone 5α-reductase inhibitors to treat various hyperandrongenic conditions including acne vulgaris, seborrhea, female hirsutism, male pattern baldness, and benign prostatic hypertrophy. This novel process may be used to oxidize or biologically transform 4-azasteroids.

The present invention is concerned with a process for biotransforming steroidal compounds including 4-azasteroids using the green algal microorganism Selenastrum capricornutum. Representative 4-azasteroids which may be oxidized by S. capricornutum include those described in U.S. Pat. Nos. 4,377,584; 4,760,071; 4,859,681; 4,845,104; 5,049,562 and 5,061,802. Advantageously, compounds of the formula:

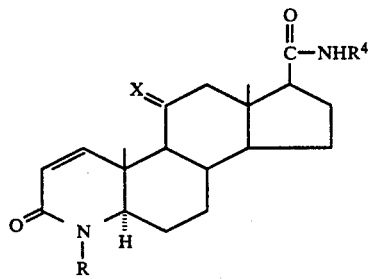

wherein

R is H, $CH_3$ or $C_2H_5$,

X is H and ($OR^3$), $R^3$ is H and $R^4$ is a branched chain alkyl of from 4–8 carbons are produced using the biotransformation process claimed in the instant invention. More advantageously, the compound 17β(N-t-butylcarbamoyl)-11α-(hydroxyl)-4-aza-5α- androst-1-en-3-one is produced using the green algal organism Selenastrum capricornutum.

Compounds produced via the claimed process are prepared by adding varying concentrations of a 4-azasteroid to cellular preparations or cultures of the commonly known and ubiquitous green algae Selenastrum capricornutum. This green algae is a unicellular or colonial organism from the Phylum Chlorophyta, Order Chlorococcales. It occurs worldwide. Selenastrum capricornutum is available at the American Type Culture Collection at 12301 Parklawn Drive, Rockville, Md. 20852 (ATCC 22662). The University of Texas at Austin also maintains a culture collection of this species (1648).

Conditions for culturing and maintaining S. capricornutum are described in the literature. The organism is readily available and may easily be cultured and maintained under a variety of conditions. See Eirkson et al., "Environmental Assessment Technical Assistance Handbook, Government Document No. PB87-175345, pp. 3–30 (1987); U.S. Environmental Protection Agency, "Algal Assay Procedure:Bottle Test", U.S. E.P.A., Corvalis, Oregon (1971); U.S. Environmental Protection Agency, "Toxic Substances Control Act Guidelines, Final Rule, Federal Register 50, 39323, 39330 (1985); Miller et al., " The Selenastrum capricornutum Printz Algal Assay Bottle Test", EPA-600/9-78-018, U.S. Environmental Protection Agency, Corvalis, Oregon (1978); and Stein, J. R., Ed. "Handbook of Phycological Methods. Culture Methods and Growth Measurements." Cambridge University Press, Cambridge, UK (1973).

The precursor 4-azasteroids (non-biotransformed precursors) used as starting materials in the process for producing the oxidized derivatives are partially soluble in the aqueous cellular system. For example, the azasteroid Finasteride (17β(N-t-butylcarbamoyl)-4-aza-5α-androst-1-en-3-one) reaches its saturation point in water at sixty(60) milligrams/liter(mg/L). The term "oxidation" in this application refers to the process of adding an oxygen atom or a hydroxyl molecule to the starting 4-azasteroids and includes oxidation at the 11-position. It further includes oxidation to the 11α (hydroxyl) compounds. Saturated solutions of the precursor azasteroids may be added to cultures of the organism *Selenastrum capricornutum* which oxidizes the respective 4-azasteroid over time to achieve substantially complete conversion of the starting material to the 11-oxo or 11-hydroxyl 4-azasteroid compounds. The temperature of the aqueous system may range between 1°-30° C. and is preferably at room temperature or 24°±2° C.

If live cultures of the organism *Selenastrum capricornutum* are used to produce the compounds produced by the claimed process, the cell batches can be monitored over daily or weekly periods to determine cell density and overall health and to ensure successful biotransformation to the target products. The term "biotransformation" retains its ordinary meaning and refers to a chemical modification of a particular molecule or biomolecule to a distinct product via the use of a microorganism such as green algae. In this specification, the term also includes cellular extracts of *Selenastrum capricornutum*, and enzymatic preparations derived therefrom, which hydroxylate or oxygenate the starting 4-azasteroids. The term "nonbiotransformed" refers to the starting steroidal compounds used in the claimed process. The term "hydroxylate" refers to hydroxylation or the addition of —OH to a carbon atom on the starting azasteroid. The term "non-hydroxylated precursor" also refers to the starting steroidal compound. The term "oxygenate" refers to oxidation of a carbon atom on the azasteroid to the respective ketone or oxygen radical or oxygen anion. It is understood that an intermediate ketone (isolated or unisolated) or stable ketone or oxygen radical or anion may be further reduced (or reacted with $H_2O$ or other hydrogen source) either in the intact cellular system, the cellular extract, or in an enzymatic preparation derived from said cells or cellular extract, to yield the hydroxyl derivative. In addition, the hydroxyl compound may be dehydrogenated to form the respective ketone.

The term enzyme or enzymatic preparation refers to oxygenases which may be responsible for adding oxygen to the 4-azasteroid substrate. The term oxygenase encompasses the well known class of enzymes, the monooxygenases which are also called hydroxylases. For example, it is known that the hydroxylase cytochrome P-450 hydroxylates corticosterone to the 11β-(hydroxyl) compound.

The term "aryl" shall mean a mono- or polycyclic system composed of 5- and 6-membered aromatic rings containing 0, 1, 2, 3 or 4 heteroatoms chosen from N, O or S and either unsubstituted or substituted with halogens, $C_{1-12}$ alkyloxy groups, or hydroxyl groups.

The term "alkyl" shall mean straight or branched chain alkane, alkene or alkyne.

The term "halogen" shall include fluorine, chlorine, bromine and iodine.

The term "oxy" shall mean an oxygen atom. The term "hydroxyl" shall mean an (OH) group.

The term "oxo" shall mean an oxygen atom attached to a carbon atom which is attached to two carbon atoms or C(CO)C.

The term "batch system" refers to a vessel to which algae, algal nutrient solution and precursor azasteroid are added whereby the algal biotransformed solution is filtered and extracted or purified by HPLC. The term "continuous flow system" refers to an enclosed packed algal bed where the in-flow contains nutrients, algae, and starting material and the "out-flow" contains essentially filled biotransformed product in solution which may then be further purified.

The algae growth and density or effects thereon may be compared to a control batch that does not contain the starting 4-azasteroid. Additional healthy cells may be added to the batch over time to ensure efficient biotransformation to the desired target compound. Algal cell concentrations may be monitored over a two week period, or longer if desired, at several day intervals. The concentration of starting azasteroid can be varied and may include either saturated or unsaturated concentrations in the particular aqueous culture system. The cell system can be monitored for both changes in cell density and growth and for changes in the morphological characteristics of the batch.

Scheme 1 illustrates the process of producing 11-oxo or 11α(hydroxyl) 4-azasteroids using the green algal organism *Selenastrum capricornutum*.

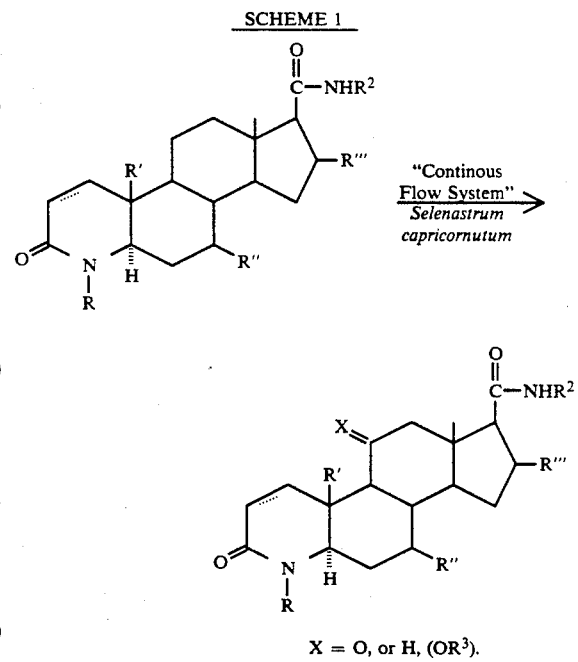

SCHEME 1

"Continous Flow System" → *Selenastrum capricornutum*

$X = O$, or $H, (OR^3)$.

Scheme 2 further illustrates the process of the instant invention.

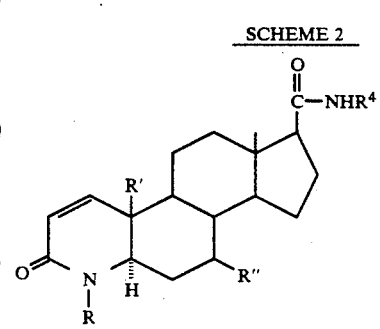

SCHEME 2

"Continous Flow System" → *Selenastrum capricornutum*

-continued
SCHEME 2

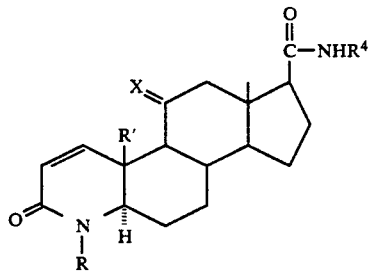

Production of the hydroxylated or oxygenated azasteroid products may be monitored by High Performance Liquid Chromatography (HPLC) over time. Production of the hydroxylated or oxygenated compounds produced in the instant invention may be monitored both by peak loss of the particular starting 4-azasteroid used and by the concommitant peak rise in the target compounds made by the claimed invention. The HPLC elution profile may show production of the oxygenated compound as the major component. Once complete loss of starting 4-azasteroid has occured or after a majority of starting compound loss has occured, the target products may readily be purified and isolated via extraction and purification technology to yield the compounds produced by the claimed invention.

In one embodiment, the aqueous algal solution from the batch system is filtered to remove cellular solids and then extracted with an organic solvent to obtain converted oxidized product.

The aqueous solution may also be passed through a solid phase cartridge ($C_{18}$ Sep-Pack) which adsorbs the target compound. This cartridge can then be flushed with methanol or other appropriate solvent to desorb the target compound.

Polypropylene cartridges or other suitable filters may be used as the filtering system. The filtered solids may be washed with a solvent such as methanol to remove any bound target compound from the cellular solids or membranes and further extracted or purified (if necessary) to obtain the target compound. Alternatively, the aqueous filtrate from the batch process may be directly purified by HPLC. Advantageously, the extract, combined extracts, or HPLC solution can be further purified by HPLC to obtain pure oxidized 4-azasteroids. The purified compounds may then be analyzed by mass spectrometry and by proton or carbon Nuclear Magnetic Resonance (NMR) to determine the structures of the target compounds. Mass spectrometry will indicate the addition of the oxygen or hydroxyl moiety. NMR will also reflect the addition of the oxygen or hydroxyl atom or molecule. The reactions and purifications can be run at any scale to achieve desired quantities of the claimed compounds.

Advantageously, compounds claimed in the instant invention may be produced in a continuous flow system. This system is initially charged with algae which pack on an enclosed solid bed. The "in-flow" initially contains nutrients to promote algal growth. When the desired biomass density is achieved, the precursor 4-azasteroid is added to the in-flow stream. The "outflow" is then monitored for biotransformed product (such as 17β-(N-t-butylcarbamoyl-11-α-(hydroxyl)-4-aza-5α-androst-1-en-3-one). The biotransformed product may readily be purified and collected at this stage. The rate or volume of in flow may also be controlled to maximize bioconversion or biotransformation. Nutrients may be added to maintain a healthy algae culture. Additional algae may be added to the in flow if necessary.

Advantageously, the compounds produced in the claimed process may be prepared by passing a saturated aqueous solution of 4-azasteroid, such as finasteride, through a large algal (*Selenastrum capricornutum*) bed situated in a continuous flow system to produce the 11-α-(hydroxyl)4-azasteroid, such as 17β(N-t-butylcarbamoyl)11α-(hydroxyl)-4-aza-5α-androst-1-en-3-one.

The reaction or biotransformation may be run at various scales to produce either small or large quantities of the 11-hydroxy azasteroids or steroidal compounds. The preferred pH is approximately 7.0 and the preferred temperature of the aqueous system is 24±2° C.

The compounds described in the instant invention, prepared in accordance with the method described above, are antiandrogens by virtue of their ability to specifically inhibit testosterone 5-α-reductase found in prostatic tissue.

Accordingly, the present invention is concerned with providing an alternative method of producing compounds which are useful in treating the hyperandrogenic conditions of acne vulgaris, seborrhea, and female hirsutism by topical administration, and useful for treating all of the above conditions as well as benign prostatic hypertrophy, by parenteral administration, of the novel compounds produced by the biotransformation process of the present invention.

The present invention is thus concerned with providing a process to produce suitable active ingredients which may be used in a topical and parenteral pharmaceutical formulation. The invention may advantageously be used to alter or diminish the biological activity of highly active testosterone 5-α reductase inhibitors (such as finasteride) so that safe non-point source or point source release of process waste streams or other environmental discharges may be achieved.

The compositions containing the compounds produced by the claimed process of the present invention as the active ingredient for use in the treatment of the various androgenic conditions may be administered in a wide variety of therapeutic dosage forms in conventional vehicles for systemic administration, as for example, by oral administration in the form of tablets, capsules, solutions, or suspensions, of by intravenous injection. Capsules containing the product of this invention can be prepared by mixing an active compound of the present invention with lactose and magnesium stearate, calcium stearate, starch, talc, or other carriers, and placing the mixture in a gelatin capsule. Tablets may be prepared by mixing the active ingredient with conventional tableting ingredients such as calcium phosphate, lactose, corn starch or magnesium stearate. The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

For the treatment of acne vulgaris, seborrhea, and female hirsutism, the compounds produced by biotransformation using the algal organism *Selenastrum ca-* pricornutum of the present invention are administered in the formula or pharmaceutical composition comprising the active compound in combination with a pharmacologically acceptable carrier adapted for topical administration. These topical pharmaceutical compositions may be in the form of a cream, ointment, gel or aerosol formulation adapted for application to the skin. These topical pharmaceutical compositions containing the compounds produced by the process of the present invention ordinarily include about 0.1% to 15% of the active compound in admixture with about 85% to 99.9% of the vehicle.

The claimed biotransformation process using the algal microorganism *Selensatrum capricornutum*, already described above in general terms, may be further illustrated by the following example.

EXAMPLE 1

Production of
17$\beta$-(N-t-butylcarbamoyl)-11$\alpha$(hydroxyl)-4-aza-5$\alpha$-androst-1-en-3-one Finasteride (17$\beta$-(N-t-butylcarbamoyl)-4-aza-5$\alpha$-androst-1-en-one), a 4-azasteroid, was added to a cellular batch of the commonly found green algal organism, *Selenastrum capricornutum* at four different concentrations: (1) 8.7 mg/L; (2) 15.5 mg/L; (3) 28.0 mg/L and (4) 49.0 mg/L (approaching saturation concentration). The biotransformation was allowed to proceed over a fourteen (14) day period in each concentration batch. A control batch was also used to monitor the algal system over the same period of time for comparative purposes.

The green algae were cultured in media prepared according to the formula described in Table 1. This forumulation is further described in Miller et al., "The *Selenastrum capricornutum* Printz Algal Assay Bottle Test." EPA-600/9-78-018. U.S. Environmental Protection Agency, Corvalis, Oreg. (1978).

TABLE 1

| Formula for the preparation of media used in the culture of the green alga, *Selenastrum capricornutum* | |
|---|---|
| Salts | Amount (g) |
| A. Macronutrients | |
| $NaNO_3$ | 12.750 |
| $MgSO_4.7H_2O$ | 7.350 |
| $K_2HPO_4$ | 0.522 |
| $NaHCO_3$ | 7.50 |
| $MgCl_2.6H_2O$ | 6.08 |
| $CaCl_2.2H_2O$ | 2.20 |
| B. Micronutrients | |
| $H_3BO_3$ | 0.0928 |
| $MnCl_2.4H_2O$ | 0.208 |
| $ZnCl_2$ | 0.00164[a] |
| $FeCl_3.6H_2O$ | 0.0799 |
| $CoCl_2.6H_2O$ | 0.000714[b] |
| $Na_2MoO_4.2H_2O$ | 0.000363[c] |
| $CuCl_2.2H_2O$ | 0.000006[d] |
| $Na_2EDTA.2H_2O$ | 0.150 |

[a]$ZnCl_2$ - Weigh out 164 mg and dilute to 100 ml. Add 1 ml of this solution to the micronutrient stock solution.
[b]$CoCl_2.6H_2O$ - Weigh out 71.4 mg and dilute to 100 ml. Add 1 ml of this solution to the micronutrient stock solution.
[c]$Na_2MoO_4.2H_2O$ - Weigh out 36.6 mg and dilute to 10 ml. Add 1 ml of this solution to the micronutrient stock solution.
[d]$CuCl_2.2H_2O$ - Weigh out 60.0 mg and dilute to 1,000 ml. Take 1 ml of this solution and dilute to 10 ml. Take 1 ml of the second dilution and add to the micronutrient stock solution.

Nutrient solutions were prepared from analytical or reagent grade chemicals as concentrated stock solutions, filter-sterilized, and stored in the dark at 4° C. Macronutrient stock solutions were prepared by dissolving the weight in grams of chemical listed in Section A of Table 1 into 500 ml of deionized water. The micronutrient stock solution was prepared in accordance with the instructions at the bottom of Table 1. Culture media was prepared by adding one ml of each macronutrient stock solution and one ml of the micronutrient stock solution to one liter of deionized laboratory tapwater. Culture media in control solutions exhibited a pH of approximately 7.0, hardness of 51 mg/L (as $CaCO_3$), alkalinity of 12 mg/L (as $CaCO_3$), and a conductivity of 210 umhos/cm.

Cultures of *S. capricornutum* were initiated daily by transferring a four-ml aliquot of an established culture (3–10 days old) to 200 ml of autoclaved media in 500-ml Erlenmeyer flasks. Cultures were incubated at a temperature of 24°+/−2° C. under continuous fluorescent lighting (400+/− foot-candles) on a shaker table. The established culture (30 mls at 7 days old) was then centrifuged to concentrate the algal cells and remove culture media. Cells were then resuspended in fresh media to determine the cell concentration. The algal cell concentration was then adjusted to approximately $10^5$ cells/ml to achieve an initial algal cell concentration of $10^3$ cells/ml in the biotransformation vessel. One ml of this algal solution was added to 99 ml of a (50 mg/L) solution of finasteride in a 250 ml flask to yield a nominal concentration of 49 mg/L. The flask was then placed on a gyratory shaker operating at 100 rpm in an environmental chamber.

A comparison of the cell concentrations in each transformation batch over time indicated no major statistical differences between cell numbers in the control or in each batch after a ten to fourteen day period. Between the first biotransformation day and the tenth day several variations in cell numbers were detected in the various concentration batches. For example, after five days cell numbers diminished in the 28 mg/L batch and in the 49 mg/L batch but cell numbers normalized to control levels after a ten day period. Algal cell densities were determined from microscopic examination of single subsamples of the cultures using a Palmer Maloney counting cell (0.1-ml capacity) and a Whipple square micrometer for enumerating algal cells. The counting procedure entailed viewing a maximum of approximately 100 Whipple square sample (represents a total of 100×100=100,000 "small squares") across the diameter of the Palmer-Maloney cell. See American Public Health Association, "Standard Methods for the Examination of Water and Wastewater, 15th Edition. American Public Health Association, Washington, D.C. (1980).

At day zero, the measured concentrations for each starting concentration was 12.0 mg/L; 14.0 mg/L; 24.0 mg/L; and 39.0 mg/L. The measured concentration of the starting component in the algal solution was determined by comparing its Ultraviolet (UV) response to the known UV response of the starting azasteroid at various prepared concentrations. The biotransformation was allowed to proceed at each concentration over a fourteen day period and after this period less than 1 mg/L of the starting compound was detected in each batch. The biotransformation reaction was monitered by HPLC and purified on $C_{18}$ Sep Pack cartridges. The elution profile after the full two week period indicated that the target compound, 17$\beta$-3-(N-t-butylcarbamoyl)-11$\alpha$-(hydroxyl)-4-aza-5$\alpha$-andros-1-en-3-one, represented (on average) 68 percent of the product blend.

17.3 Micrograms of the above 11α-(hydroxyl)azasteroid was isolated, purified, and characterized.

Thermospray (TSP) mass spectroscopy was performed on the major biotransformation product. The results indicated a molecular ion [M+H]+ at m/z 389 which is 16 atomic units greater than the starting reactant's (finasteride) molecular ion of m/z 373 [M+H]+. 16 atomic units or Daltons (Da) is the molecular weight of an additional oxygen atom. Proton ($^1$H) NMR was used to confirm the location (carbon atom point of attachment on the azasteroid skeleton) and stereoposition (alpha or beta, where the 17-beta position is defined as the axial position of a classical steroidal structure and the 17-alpha position is defined as the equatorial position on the same steroidal three dimensional skeleton) of the hydroxyl molecule on the biotransformed product. $^1$H NMR showed a new HC-OH multiplet at 4.09 ppm relative to the starting reactant's NMR spectrum. In addition, downfield shifts of 1.10 parts per million (ppm) for the C-1 hydrogen and 0.11 ppm for the C-19 hydrogens occurred relative to the starting material. The downfield displacements were indicative of a new nearby substituent. These results demonstrated that the hydroxylation had occured at the 11 position. If hydroxylation had occured at the alternative nearby position, the six position, then the normal C-5 hydrogen would appear with reduced multiplicity and would be displaced downfield. In fact, the C-5 hydrogen signal was unchanged. Likewise, if hydroxylation had occured at the C-9 position, then the new multiplet at 4.09 ppm would not have appeared. The 11α configuration for the hydroxyl was indicated because of the modest 0.1 ppm displacement of the C-19 signal and the unchanged chemical shift for the hydrogens on C-18 relative to spectrum for the starting azasteroid finasteride. An 11β hydroxyl causes a 0.25 ppm downfield displacement of both angular(axial) methyl peaks. The biotransformed product, 17β(N-t-butylcarbamoyl)-11α-(hydroxyl)-4-aza-5α-androst-1-en-3-one, demonstrated inhibition of the prostate enzyme testosterone 5α-reductase.

The above example is not intended to limit the scope or application of the claimed invention. The quantities of starting 4-azasteroid and of the algal bed may be modified to various levels, including production levels, to produce the oxidized or hydroxylated compounds using the green algae Selenastrum capricornutum. Large scale HPLC systems or factory scale extraction and purification equipment may be used to purify and obtain the products produced by the claimed process.

What is claimed is:

1. A process for 11α-hydroxylating steroidal compound comprising the step of contacting said steroidal compound with a green algae, Selenastrum capricornutum in an aqueous system at a pH of approximately 7 and a temperature of 1°-30° C.

2. A process for making an 11α-hydroxylated oxygenated 4-azasteroid according to claim 1 comprising contacting a 4-azasteroid with said green algae, Selenastrum capricornutum.

3. A process for making an 11α-hydroxylated 4-azasteroid according to claim 1 comprising contacting a saturated solution of non-biotransformed 4-azasteroid with said organism, Selenastrum capricornutum.

4. A process according to claim 1 for making a compound of the formula:

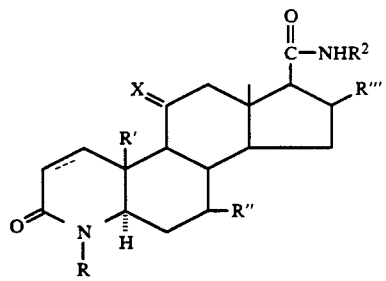

wherein the dashed line indicates a double bond may be present;

R is hydrogen, methyl, or ethyl;

R$^2$ is a hydrocarbon selected from straight and monocyclic aryl optionally containing 1 or more lower alkyl substituents of from 1-2 carbon atoms and/or more halogen substituents;

R' is hydrogen or methyl;

R'' is hydrogen or β-methyl;

R''' is hydrogen, α-methyl or β-methyl;

X is H and (OR$^3$) wherein R$^3$ is H, c$_{1-13}$.

5. A process according to claim 1 for making a compound of the formula

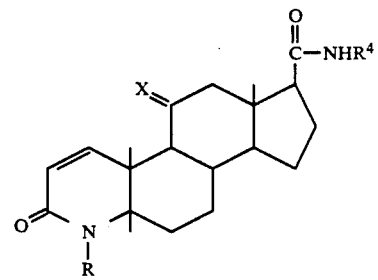

wherein

R is H, CH$_3$ or C$_2$H$_5$;

X is H and (OR$^3$) wherein R$^3$ is H;

R$^4$ is a branched chain alkyl of from 4-8 carbons.

6. A process according to claim 1 for making a compound of the formula:

17β-(N-tertbutylcarbamoyl)-11α-(hydroxyl)-4-aza-4-methyl-5α-androst-1-en-3-one;

17β-(N-isobutylcarbamoyl)-11α-(hydroxyl)-4-aza-4-methyl-5α-androst-1-en-3-one;

17β-(N-tertoxtylcarbamoyl)-11α-(hydroxyl)-4-aza-4-methyl-5α-androst-1-en-3-one;

17β-(N-octylcarbamoyl)-11α-(hydroxyl)-4-aza-4-methyl-5α-androst-1-en-3-one;

17β-(N-diethylbutylcarbamoyl)-11α-(hydroxyl)-4-aza-4-methyl-5α-androst-1-en-3-one;

17β-(N-neopentylcarbamoyl)-11α-(hydroxyl)-4-aza-4-methyl-5α-androst-1-en-3-one;

17β-(N-tertamylcarbamoyl)-11α-(hydroxyl)-4-aza-4-methyl-5α-androst-1-en-3-one;

17β-(N-terthexylcarbamoyl)-11α-(hydroxyl)-4-aza-4-methyl-5α-androst-1-en-3-one, comprising contacting a non-hydroxylated precursor 4-azasteroid with said algal organism, Selenastrum capricornutum.

7. A process according to claim 1 comprising 11α-hydroxylation of 17β(N-t-butylcarbamoyl)-4-aza-5α-androst-1-en-3-one using said green algae Selenastrum capricornutum to produce 17β(N-t-butylcarbamoyl)-11α(hydroxyl)-4-aza-5α-androst-1-en-3-one.

* * * * *